United States Patent
Terradas Camins et al.

(10) Patent No.: US 10,888,500 B2
(45) Date of Patent: Jan. 12, 2021

(54) PARTICLE SIZE STABILIZATION PROCESS

(71) Applicant: INKE, S.A., Castellbisbal-Barcelona (ES)

(72) Inventors: Josep Terradas Camins, Castellbisbal-Barcelona (ES); Josep Maria Carulla Oliver, Castellbisbal-Barcelona (ES); Silvia Donnici Garcia, Castellbisbal-Barcelona (ES); David Gomez Lamarca, Castellbisbal-Barcelona (ES); Maria Jose Martinez Velon, Sant Joan Despi-Barcelona (ES); Emma Recio Soler, Sant Joan Despi (ES)

(73) Assignee: INKE, S.A., Castellbisbal (ES)

( * ) Notice: Subject to any disclaimer, the term of this patent is extended or adjusted under 35 U.S.C. 154(b) by 0 days.

(21) Appl. No.: 16/321,034

(22) PCT Filed: Jul. 25, 2017

(86) PCT No.: PCT/EP2017/068707
§ 371 (c)(1),
(2) Date: Jan. 27, 2019

(87) PCT Pub. No.: WO2018/019803
PCT Pub. Date: Feb. 1, 2018

(65) Prior Publication Data
US 2019/0175451 A1   Jun. 13, 2019

(30) Foreign Application Priority Data
Jul. 29, 2016   (EP) ..................... 16382374

(51) Int. Cl.
| | |
|---|---|
| *A61J 3/02* | (2006.01) |
| *A61K 9/00* | (2006.01) |
| *A61K 9/14* | (2006.01) |
| *A61K 31/40* | (2006.01) |
| *A61K 31/4015* | (2006.01) |
| *A61K 45/06* | (2006.01) |

(52) U.S. Cl.
CPC ............... *A61J 3/02* (2013.01); *A61K 9/0075* (2013.01); *A61K 9/14* (2013.01); *A61K 31/40* (2013.01); *A61K 31/4015* (2013.01); *A61K 45/06* (2013.01)

(58) Field of Classification Search
CPC ......... A61J 3/02; A61K 31/40; A61K 9/0075; A61K 9/14; A61P 11/06
See application file for complete search history.

(56) References Cited

U.S. PATENT DOCUMENTS

| | | | |
|---|---|---|---|
| 2,956,062 A | 10/1960 | Lunsford | |
| 9,393,202 B2 * | 7/2016 | Pasquali | ............. A61K 9/0075 |
| 2014/0275517 A1 | 9/2014 | Kazmi et al. | |

FOREIGN PATENT DOCUMENTS

| | | |
|---|---|---|
| EP | 2422766 A2 | 2/2012 |
| EP | 2422767 A2 | 2/2012 |
| WO | WO2005105043 A2 | 11/2005 |
| WO | WO200907666 A1 | 6/2009 |
| WO | WO-2009074662 A2 * | 6/2009 ............. A61K 9/008 |
| WO | WO2009074662 A2 | 6/2009 |
| WO | WO2016102174 A1 | 6/2016 |

OTHER PUBLICATIONS

Hosokawa (https://cdn.thomasnet.com/ccp/00594184/272248.pdf) 2010, pp. 1-19 (Year: 2010).*
Depalma, A. "Vacuum Pumps: The Widest Dynamic Range of Any Lab Device" (https://www.labmanager.com/product-focus/vacuum-pumps-the-widest-dynamic-range-of-any-lab-device-19174) Nov. 9, 2010, pp. 1-5 (Year: 2010).*

* cited by examiner

*Primary Examiner* — Andrew S Rosenthal
(74) *Attorney, Agent, or Firm* — Hulquist, PLLC; Steven J. Hulquist

(57) ABSTRACT

The present invention provides a new process for stabilizing the particle size of micronized glycopyrronium salt (such as glycopyrronium bromide) which yields a micronized product exhibiting improved chemical and polymorphic stability even after prolonged storage. The invention also relates to compositions comprising said stabilized glycopyrronium salt (such as glycopyrronium bromide) and to dry powder inhaler devices and capsules or blisters comprising the stabilized glycopyrronium salt (such as glycopyrronium bromide). The glycopyrronium salt (such as glycopyrronium bromide) or compositions of the invention may be used as a medicament, for instance in the treatment of asthma, chronic obstructive pulmonary disease or cystic fibrosis or related diseases.

18 Claims, 4 Drawing Sheets

| Angle (2-theta) | d value (Angstrom) | Relative Intensity % |
|---|---|---|
| 5.3 | 16.74 | 31.8 |
| 10.6 | 8.33 | 21.3 |
| 14.2 | 6.22 | 53.0 |
| 15.7 | 5.65 | 64.7 |
| 18.4 | 4.81 | 71.5 |
| 19.2 | 4.62 | 85.0 |
| 19.9 | 4.46 | 36.1 |
| 20.0 | 4.43 | 10.4 |
| 21.4 | 4.15 | 54.0 |
| 21.8 | 4.07 | 11.5 |
| 21.9 | 4.05 | 13.4 |
| 24.2 | 3.68 | 100.0 |
| 24.5 | 3.63 | 28.1 |
| 25.0 | 3.55 | 32.6 |
| 25.6 | 3.47 | 10.4 |
| 27.3 | 3.27 | 13.8 |
| 28.4 | 3.14 | 17.3 |
| 29.3 | 3.04 | 19.4 |
| 29.7 | 3.00 | 13.3 |
| 29.9 | 2.99 | 12.6 |
| 30.1 | 2.96 | 15.5 |
| 30.6 | 2.92 | 34.3 |
| 30.8 | 2.90 | 28.4 |
| 32.7 | 2.74 | 12.5 |
| 36.2 | 2.48 | 13.4 |
| 38.2 | 2.36 | 11.3 |

PARTICLE SIZE STABILIZATION PROCESS

CROSS-REFERENCE TO RELATED APPLICATIONS

This application is a U.S. national phase under 35 U.S.C. § 371 of International Patent Application No. PCT/EP17/68707 filed Jul. 25, 2017, which in turn claims priority of European Patent Application No. 16382374.3 filed Jul. 29, 2016. The disclosures of such International Patent Application No. PCT/EP17/68707 and European Patent Application No. 16382374.3 are hereby incorporated herein by reference in their respective entireties, for all purposes.

FIELD OF THE INVENTION

The present invention provides a new process for stabilizing the particle size of micronized glycopyrronium salt (such as glycopyrronium bromide) which yields a micronized product exhibiting improved chemical and polymorphic stability, even after prolonged storage. The invention also relates to compositions comprising said stabilized glycopyrronium bromide and to dry powder inhaler devices and capsules or blisters comprising the stabilized glycopyrronium salt (such as glycopyrronium bromide). The glycopyrronium salt (such as glycopyrronium bromide) or compositions of the invention may be used as a medicament, for instance in the treatment of asthma, chronic obstructive pulmonary disease or cystic fibrosis or related diseases.

BACKGROUND OF THE INVENTION (3RS)-3-[(2SR)-(2-cyclopentyl-2-hydroxy-2-phenylacetyl)oxy]-1,1-dimethylpyrrolidinium bromide, also known as glycopyrronium bromide (depicted below as Compound I) is an M3 antagonist, developed by Sosei R&D in collaboration with Vectura for the treatment of chronic obstructive pulmonary disease (COPD) and asthma.

Compound I

Glycopyrronium bromide, sometimes also referred to as glycopyrrolate, is a quaternary ammonium salt (ionic compound) that is completely ionized between pH 1 and 14. It is a racemic mixture of the 3R,2S and 3S,2R stereoisomers. No optical rotation is seen in solution. Glycopyrronium bromide is inter alia marketed under the tradename Robinul®, Seebri® Breezhaler®, or Ultibro® Breezhaler®.

Glycopyrronium bromide was first disclosed in U.S. Pat. No. 2,956,062, which describes a synthetic approach for the preparation of glycopyrronium bromide, similar molecules and also pharmaceutical compositions containing them.

As noted above, glycopyrronium bromide is useful in the treatment of respiratory diseases such as asthma, chronic pulmonary disease (COPD), cystic fibrosis (CF) and other related diseases. In the treatment of airway diseases, drugs are preferably administered locally, e.g. by inhalation, in order to avoid adverse systemic side effects. Glycopyrronium bromide may be provided in the form of dry powder formulations, thereby enabling the application using dry powder inhalers.

However, if dry powder formulations are to be delivered to the respiratory airways, particles must be of a particular (small) size in order to reach their intended site of action as particles which are too big will be deposited in the mouth and do not reach the lung. Usually, source powders of drugs exist in particle sizes that are not sufficiently small to be administered by inhalation. Therefore micronization is frequently used to reduce the size of the primary particles to a particle size which is suitable for inhalation. However, micronization of drugs, e.g. by milling or grinding may considerably alter the physicochemical properties of the drug and thus impede formulation of suitable dosage forms or alter bioavailability of the drug.

Accordingly, micronized glycopyrronium bromide may exhibit stability problems, particularly upon storage, mainly due to aggregation and/or agglomeration of the fine micronized drug particles. Aggregated or agglomerated particles present in the formulation may considerably reduce the amount of drug available at the site of action. Further, micronization may also lead to the generation of unfavorable non-crystalline, i.e. amorphous material which is hygroscopic (which in turn may also favor agglomeration).

Stabilization of micronized drugs is therefore crucial in order to ensure that the same amount of drug is applied per dose. Accordingly, there is a need in the art for dry powder formulations consisting of particles of a suitable size which are stable over a prolonged period of time, i.e. which do not contain any significant amounts of amorphous glycopyrronium bromide and which do not form aggregates or agglomerates upon storage.

Several methods to stabilize micronized glycopyrronium bromide in order to avoid aggregation and/or agglomeration and the occurrence of amorphous material have been described in the prior art.

Some applications describe methods for the generation of stable micronized glycopyrronium bromide which are based on exposure to humid conditions. For example, EP2422767 B1 describes formulations comprising micronized glycopyrronium bromide that underwent a conditioning step including exposure to humid conditions of 30-100% relative humidity at temperatures between 5° C. to 90° C. for at least 48 hours. EP1755555 B1 discloses a method for producing pharmaceutical compositions suitable for inhalation comprising micronized glycopyrrolate and magnesium stearate, which comprises a conditioning step including exposure to humid conditions.

EP2229148 B1 refers to an alternative process for stabilizing micronized glycopyrronium bromide by using high pressure homogenization. Dispersing the powder in an antisolvent, homogenization at an elevated pressure of between 500 and 2000 bar and subsequent drying yielded a substantially pure and crystalline drug substance which retained a stable particle size over time.

EP2234595 B1 discloses a different approach for reducing the tendency of micronized glycopyrronium salt to aggregate and/or agglomerate during storage which is based on a heating step to a temperature of between 40 and 120° C. for at least 6 hours. More specifically, in the working examples the co-micronized glycopyrronium salt and magnesium stearate was exposed to a dry environment at a temperature of 70° C. for 48 hours.

There is a need in the art for further economic and reliable processes that are capable of producing stabilized glycopyrronium salts in micronized form.

SUMMARY OF THE INVENTION

The inventors of the present invention have surprisingly found that further increasing the temperature during the curing step (a thermal treatment, i.e. heating) to a range from about 125° C. to about 160° C. for at least about 2 hours considerably improved the chemical and polymorphic stability of the micronized glycopyrronium salts (such as glycopyrronium bromide). Moreover, it was found that the stabilized micronized glycopyrronium salt produced by the method of the invention exhibited enhanced physicochemical stability upon storage over a prolonged period of time without apparent changes in the particle size distribution (which would indicate possible agglomeration or aggregation of smaller particles). Likewise, it was found that the stabilized micronized glycopyrronium salts did not show any significant content of amorphous drug material, even after prolonged storage at 25° C. The term "prolonged" used herein is defined as at least 1 month, preferable at least 2 months and most preferably 3 months.

Accordingly, the present invention relates in a first aspect to a process for obtaining a stable glycopyrronium salt comprising the steps of micronizing the glycopyrronium salt, optionally in the presence of one or more other active ingredients and/or excipients, to obtain a particle size distribution (PSD) characterized by a $D_{90}$ of equal to or below about 10 µm and then curing the micronized glycopyrronium salt by maintaining the product for at least 2 hours at a temperature of between about 125° C. and about 160° C.

In another aspect, the present invention provides a glycopyrronium salt having a particle size distribution characterized by a $D_{90}$ of equal to or below about 10 µm, and further characterized in that its particle size remains stable after 1 month of storage at 25° C., preferably after 2 months of storage at 25° C. and most preferably after 3 months of storage at 25° C., optionally wherein the $D_{90}$ value does not increase by more than 15%, or by more than 5% after 1 month of storage at 25° C., preferably after 2 months of storage at 25° C. and most preferably after 3 months of storage at 25° C.

Compositions comprising the glycopyrronium salt as well as dry powder inhaler devices or capsules or blisters suitable for such dry powder inhaler devices represent another aspect of the present invention.

The glycopyrronium salt in all of these aspects is preferably glycopyrronium bromide.

DETAILED DESCRIPTION OF THE INVENTION

Definitions

The term "micronization" as used herein refers to the process of reducing the average diameter of a solid material's particles. Usually, the term micronization is used when the particles that are produced are only a few micrometres (typically less than 10 µm) in diameter. Traditional micronization techniques are based on the use of friction to reduce particle size. Such methods include milling and grinding. Reduction in particle size may also take place as a result of collision and impact of the particles to each other.

The term "curing" as used herein refers to a thermal treatment which is carried out after micronizing glycopyrronium salt.

The term "about" when used in connection with a value (i.e. about 10) is meant to designate a range around the value specified ±10%, preferably ±5%, more preferably ±3% and still more preferably ±1%. As a mere example the fragment "about 100° C." would be construed to mean 90-110° C., preferably 95-105° C., more preferably 97-103° C. and still more preferably 99-101° C.

The term "$D_X$" as used herein means that x % of the particles in a composition (based on volume) have a diameter of equal to or below a specified D value. Thus, a $D_{90}$ of 10 µm means that 90% of the particles, by volume, have a diameter of or below 10 µm. As well as using $D_{90}$ as a measuring reference to determine particle size, $D_{50}$ is sometimes used for such a purpose. Therefore, a $D_{50}$ of 5 µm means that 50% of the particle population, by volume, have a diameter of equal to or below 5 µm.

The term "room temperature" (or "RT") in the present context means a temperature from generally about 15° C. to about 30° C., typically from 20° C. to 30° C.

The term "stabilizing" as used herein refers to a process for ensuring or improving the stability of the micronized glycopyrronium salts so as to generate a (chemically as well as polymorphically) stable product.

The term "stable" as used herein refers to micronized glycopyrronium salts which do not agglomerate and/or aggregate. In particular "stable" is used to refer to micronized glycopyrronium salts whose particle size distribution (expressed by its $D_{90}$ value) does not increase by more than 15% after storage under defined and controlled conditions, such as 25° C. Preferably, the product is stored at 25° C. under vacuum conditions, or at 25° C. under nitrogen atmosphere or at atmospheric conditions (25° C. and 60% RH) packed in an aluminum bag tightly sealed. The term stable in the context of micronized glycopyrronium salts preferably refers to a product whose particles do not agglomerate and/or aggregate, and whose particle size distribution (expressed by its $D_{90}$ value) does not increase by more than 15%.

When the stability studies are carried out in accordance to ICH guidelines Q1A the samples are packed in an aluminum bag tightly sealed and stored in a controlled chamber which is maintained at 25° C.±2° C. and 60% RH±5% RH and periodically controlled for stability purposes.

The term "polymorphically stable" as used herein means that the glycopyrronium salt does not evolve to contain more or equal to 1 wt. % of amorphous glycopyrronium salt as analyzed by DVS (Dinamic Vapor Sorption)

The term "prolonged" employed herein refers to a period of at least 1 month, or at least 2 months, or at least 3 months.

The term "excipient" as used herein means any pharmaceutically acceptable excipient. Preferably the excipient is a material that is capable of reducing the tendency for the drug substance to aggregate or agglomerate. Potential excipients to be used in the context of the present invention may include crystalline sugars such as lactose and glucose, fatty acid derivatives such as magnesium stearate or calcium stearate, amino acids such as leucine, or phospholipids such as lecithin. Surface-active substances or polymers such as poloxamer, cellulose ethers, PVA, PVP and the like may also be included.

Embodiments of the Invention

In a first aspect, the present invention relates to a process for obtaining a stable micronized glycopyrronium salt comprising the steps of micronizing a glycopyrronium salt to obtain a particle size distribution (PSD) characterized by a $D_{90}$ of equal to or below about 10 μm (step (a)), and curing the micronized glycopyrronium salt by maintaining the product for at least 2 hours at a temperature of between about 125° C. and about 160° C. (step (b)).

Thus, the curing step according to the present invention can be defined as a thermal treatment after micronizing the glycopyrronium salt, which is typically conducted on trays in a suitable oven at a temperature between about 125° C. and about 160° C. over at least 2 hours.

Preferably, the glycopyrronium salt is glycopyrronium bromide, although the process can of course also be carried out with other glycopyrronium salts described in the art.

Typically, the desired particle size is achieved after one micronization step. However, in certain embodiments, the desired particle size may also be achieved after more than one, such as two or three micronization steps.

In some embodiments, the micronization of the glycopyrronium salt in step a) is carried out on its own, i.e. in the absence of any excipient or other active ingredient. The micronization of the glycopyrronium salt may also be carried out in the presence of one or more other active ingredients, and/or one or more excipients, which are preferably pharmaceutically acceptable excipients.

Potential other active ingredients in this context may be selected from β2-agonists, glucocorticoids, anticholinergic drugs and phosphodiesterase inhibitors or other drugs which may be administered in combination with glycopyrronium bromide. Moreover, pharmaceutically acceptable excipients, e.g. magnesium stearate or lactose, may be added, for example in order to further reduce the tendency of the product to aggregate or agglomerate.

In certain embodiments, the micronization step a) is carried out until the glycopyrronium salt, such as glycopyrronium bromide, has a particle size distribution (PSD) characterized by a $D_{90}$ value of equal to or below 8 μm. Preferably, the micronization step a) is carried out until the glycopyrronium salt has a $D_{90}$ of equal to or below 6 μm, or until the glycopyrronium salt has a $D_{90}$ of equal to or below 5 μm or equal to or below 4 μm.

In certain embodiments, the micronization of step a) is carried out until the glycopyrronium bromide has a $D_{50}$ of equal to or below 6 μm, preferably until the glycopyrronium bromide has a $D_{50}$ of equal to or below 5 μm, 4 μm, 3 μm, or 2 μm.

In other embodiments the micronization step a) is carried out until the glycopyrronium salt, such as glycopyrronium bromide, has a particle size distribution (PSD) characterized by a $D_{90}$ value equal to or below 8 μm, preferably equal to or below 6 μm, preferably equal to or below 5 μm and most preferably equal to or below 4 μm and a $D_{50}$ equal to or below 6 μm, preferably equal to or below 5 μm, more preferably equal to or below 4 μm, more preferably equal to or below 3 μm and most preferably equal to or below 2 μm.

The micronization of step a) is typically carried out at increased pressure. Accordingly, in some embodiments, the micronization is carried out at a pressure of up to 8 bar. Alternatively, the micronization of step a) is carried out at a pressure of up to about 5 bar, or up to about 4 bar.

Within the scope of the present invention the carrier gas used in the micronization process may, for example, be air, dehumidified air, dry oil-free air, noble gases, nitrogen or mixtures thereof.

Alternatively or in addition, the micronization step a) is typically carried out at a temperature of between −10° C. and 30° C., or at a temperature of between 10° C. and 25° C., or at room temperature. Given that glycopyrronium salts are relatively stable, the micronization step a) is preferably carried out at room temperature. The term "room temperature" in the context of the curing step means that the temperature is between 15-30° C.

The particle size distribution may slightly vary and usually slightly decrease after the curing process due to the surface stabilization of the crystalline drug substance. This variation in the particle size distribution is usually not more than ±10%. Preferably, not more than ±5%. Most preferably not more than ±4%.

In some embodiments, the micronized glycopyrronium salt is maintained in the curing step b) at a temperature of between about 125° C. and about 160° C. for at least 3 hours, or at least 4 hours, or at least 5 hours or at least 6 hours. The micronized glycopyrronium salt may also be maintained in the oven for at least 12 hours, optionally for at least 24 hours.

While longer exposure to these temperatures are generally possible, the working examples show that exposure of the micronized glycopyrronium salt to heating for less than 6 or even less than 4 hours is sufficient to obtain a stabilized micronized glycopyrronium salt. Accordingly, in preferred embodiments, the micronized glycopyrronium salt is maintained in the curing step b) at a temperature of between about 125° C. and about 160° C. for at least 2 hours but not more than about 6 hours, or not more than about 4 hours.

Preferably, the temperature in curing step b) is maintained between 125° C. and 150° C., or between 130° C. and 150° C., or between 130° C. and 140° C., e.g. 130° C.

Preferably, the micronized glycopyrronium salt is maintained in the oven for at least 2 hours, more preferably for at least 4 hours, most preferably for at least 6 hours.

Typically, the curing step b) is carried out either at atmospheric pressure, or under reduced pressure, principally ranging from 0 (or as close to 0 as technically feasible, such as below 50 mbar or below 20 mbar) to below 1 atm. For example, the curing step b) may be carried out under reduced pressure of below 500 mbar, below 200 mbar, or below 100 mbar or below 50 mbar. In a particularly preferred embodiment, the curing step b) is carried out under vacuum conditions, with vacuum being defined for practical reasons at below 50 mbar, or below 20 mbar.

In another aspect, the invention also refers to a stabilized, typically crystalline, glycopyrronium salt having a particle size distribution characterized by a $D_{90}$ of equal to or below about 10 µm, and further characterized in that its particle size remains stable after 1 month of storage, or after 2 months of storage, or after 3 months of storage at 25° C. Thus, in certain embodiments, the glycopyrronium salt may be defined by showing no tendency to agglomerate or aggregate, even after 1 month of storage, or after 2 months of storage, or after 3 months of storage at 25° C. Preferably, the product is stored at 25° C. under vacuum conditions, or at 25° C. under nitrogen atmosphere or at atmospheric conditions (25° C. and 60% RH) packed in an aluminum bag tightly sealed.

Preferably, the glycopyrronium salt is glycopyrronium bromide. When glycopirronium bromide is used, it can be obtained as for the process of WO2016102174 or as disclosed by the U.S. Pat. No. 2,956,062 to Robins Company.

In some embodiments, the $D_{90}$ value of the stabilized glycopyrronium salt according to the invention is equal to or below 10 µm and does not increase by more than 15%, or by more than 10% or by more than 5% after 1 month of storage, or after 2 months of storage, or after 3 months of storage at 25° C. Preferably the $D_{90}$ value of the stabilized glycopyrronium salt according to the invention does not increase by more than 10% after 1 month of storage at 25° C. Preferably, the product is stored under vacuum conditions, or at 25° C. under nitrogen atmosphere or at atmospheric conditions (25° C. and 60% RH) when is packed in an aluminum bag tightly sealed.

The glycopyrronium salt has preferably a particle size distribution (PSD) characterized by a $D_{90}$ of equal to or below about 8 µm, more preferably of equal to or below about 6 µm, most preferably of equal to or below about 5 µm or below about 4 µm.

In some embodiments of this aspect of the invention, the invention relates to a crystalline glycopyrronium salt which is further characterized by having a content of an amorphous form of said glycopyrronium salt, as determined by dynamic vapor sorption (DVS), of less than about 1.2%, or less than about 1.0%, or less than about 0.8%, or less than about 0.6%.

The stabilized glycopyrronium salt according to the invention is preferably chemically and polymorphically stable, even after 1 month of storage, or after 2 months of storage, or after 3 months of storage at 25° C. Preferably, the product is stored at 25° C. under vacuum conditions, or at 25° C. under nitrogen atmosphere or at atmospheric conditions (25° C. and 60% RH) packed in an aluminum bag tightly sealed.

In some embodiments, the glycopyrronium salt according to the present invention is chemically and polymorphically stable after 1 month of storage at 25° C. Preferably, the product is stored at 25° C. under vacuum conditions, or at 25° C. under nitrogen atmosphere or at atmospheric conditions (25° C. and 60% RH) packed in an aluminum bag tightly sealed. In other preferred embodiments, the glycopyrronium salt of the invention is chemically and polymorphically stable after 2 months of storage under the same conditions. In a particularly preferred embodiment, the glycopyrronium salt of the present invention is chemically and polymorphically stable after 3 months of storage.

In certain embodiments, the purity of the compound is not lower than 99.5 wt. %, preferably not lower than 99.7 wt. % and most preferably not lower than 99.9 wt. %, i.e. the amount of impurities after 1 month of storage at 25° C., preferably after 2 months of storage at 25° C. and most preferably after 3 months of storage at 25° C. is equal to or below about 0.5 wt. %, or 0.3 wt. %, or wt. 0.1%. In a preferred embodiment, the purity of the compound is not lower than 99.9 wt. % after 1 month of storage at 25° C. not lower than 99.5 wt. % after 3 months, i.e. the amount of impurities is equal to or below about 0.1 wt % after 1 month of storage and/or equal to or below about 0.5 wt. % after 3 months of storage at 25° C. Preferably, the product is stored at 25° C. under vacuum conditions, or at 25° C. under nitrogen atmosphere or at atmospheric conditions (25° C. and 60% RH) packed in an aluminum bag tightly sealed.

The glycopyrronium salt according to this aspect of the invention has preferably been micronized. In certain embodiments, the glycopyrronium salt according to the present invention has been micronized in the absence of other active ingredients or excipients. Alternatively, the glycopyrronium salt according to the invention has been micronized in the presence of one or more other active ingredients and/or excipients. Preferably, the glycopyrronium salt is glycopyrronium bromide.

In yet another aspect, the present invention relates to a glycopyrronium salt, such as glycopyrronium bromide, obtainable by a process as described herein. In some embodiments, the glycopyrronium salt obtainable by the process according to the invention is as defined herein above. Preferably, the glycopyrronium salt is glycopyrronium bromide.

Moreover, the present invention also relates to compositions comprising the stabilized glycopyrronium salt according to the present invention. Optionally, compositions according to this aspect of the present invention may further comprise, in addition to the glycopyrronium salt, one or more further active ingredients and/or excipients as described above. Preferably, the glycopyrronium salt is glycopyrronium bromide.

Yet another aspect of the present invention relates to a stabilized glycopyrronium salt, such as glycopyrronium bromide, or a composition comprising said glycopyrronium salt as described herein for use as a medicament. Preferably, the present invention discloses the stabilized glycopyrronium salt or the composition according to the present invention for use in treating an airway disease, for instance asthma, COPD, cystic fibrosis, or related diseases. Preferably, the glycopyrronium salt is glycopyrronium bromide.

Finally, in a further aspect, the present invention also relates to a dry powder inhaler device, or a capsule or blister suitable for a dry powder inhaler device, comprising the stabilized glycopyrronium salt (such as glycopyrronium bromide) or the composition comprising said stabilized glycopyrronium salt as described herein.

Having described the various aspects of the present invention in general terms, it will be apparent to those of skill in the art that many modifications and slight variations are possible without departing from the spirit and scope of the present invention.

Experimental Methods

The compounds of the present invention were characterized by common analytical techniques such as Powder X-Ray Diffraction (PXRD), Dynamic Vapor Sorption Analysis (DVS) and Laser Diffraction Spectrometry (LDS) using the following methods:

Powder X-Ray Diffraction (PXRD) Analysis:

Approximately 15 mg of non-manipulated sample were prepared in standard sample holders using two foils of polyacetate. Powder diffraction patterns were acquired on a D8 Advance Series 2-Theta/Theta powder diffraction system using CuK$_{\alpha 1}$-radiation in transmission geometry. The system is equipped with a VÅNTEC-1 single photon counting PSD, a Germanium monochromator, a ninety positions auto changer sample stage, fixed divergence slits and a radial soller. Programs used: Data collection with DIFFRAC plus XRD Commander V.2.5.1, and evaluation and area integration with EVA V.14.0.0.0 (Bruker-AXS 1996-2007). The samples were measured in a range from 4° to 40° in 2 theta in 10 minutes or 1 hour measurements.

X-ray crystal structures (SCXRD) were determined as follows: Data collection: The measured crystals were prepared under inert conditions and immersed in perfluoropolyether as protecting oil for manipulation. Crystal structure determinations were carried out using an Apex DUO Kappa 4-axis goniometer equipped with an APPEX 2 4K CCD area detector, a Microfocus Source E025 IuS using MoK$_\alpha$ radiation (0.71073 Å), Quazar MX multilayer Optics as monochromator and an Oxford Cryosystems low temperature device Cryostream 700 plus (T=−173° C.). Full-sphere data collection was used with ω and φ scans. Programs used: Data collection APEX-21, data reduction Bruker Saint2 V/0.60 A and absorption correction TWINABS3.

Structure Solution and Refinement: Crystal structure solution was achieved using direct methods as implemented in SHELXTL4 and visualized using the program XP. Missing atoms were subsequently located from difference Fourier synthesis and added to the atom list. Least-squares refinement on F2 using all measured intensities was carried out using the program SHELXTL. All non-hydrogen atoms were refined including anisotropic displacement parameters.

Dynamic Vapor Sorption Analysis (DVS):

The experiments were performed in a Mettler Toledo TGA/DSC 1 LF instrument equipped with a LF SDTA FRS2 sensor and coupled with a Modular Humidity Generator MHG 32. The samples were weighted into 150 µL platinum crucibles. Data collection and evaluation was done with STARe software. A water uptake method was used to determine the amorphous content. In this method, the relative mass difference at a specific relative humidity (20%) prior to and post humidity-induced crystallization was compared. Assuming no solvate or hydrate formation, the difference in uptake between partially amorphous and recrystallized material is directly proportional to the initial amount of amorphous material in the sample. A purely amorphous sample (reference sample) was used as amorphous standard. The water uptake of a sample is proportional to the amount of amorphous content present in the sample.

Laser Diffraction Spectrometry (LDS) was used to determine the Particle Size Distribution (PSD) and the determination of the presence of aggregates.

Particle Size Distribution (SYMPATEC).

The particle size distribution of sample was measured by using a Helos particle size analyser using a R1 lense with an Aspiros feeder using a dispersing dry process on 50 mg of glycopyrronium salt product.

Determination of Presence of Aggregates (MALVERN).

The presence of aggregates in a sample was determined by using a Malvern Mastersizer 2000 instrument. For example: 100 mg of glycopyrronium salt were mixed with 5 ml of a previously prepared saturated solution of glycopyrronium salt in n-heptane containing 0.2 wt. % of Span-20. Ultrasonic treatment of the samples was performed for 2 minutes.

EXAMPLES

The following non-limiting working examples further illustrate certain embodiments of the present invention. It will be understood that the micronization process of crystalline glycopyrronium bromide typically takes place with a partial retention of the product in the micronizer. Thus, the amount and yield of the product recovered from the micronization process generally depends on the type of micronizer and has therefore not been specified in the following working examples.

Example 1 (Comparative Example): Preparation of Glycopyrronium Bromide 400 g of crystalline glycopyrronium bromide was micronized at room temperature (15-30° C.) in an ALPINE Pharma Multi-Processing System 100 AFG/100 AS micronizer with integrated GLOVE-BOX at a micronization pressure of 5 bar obtaining a particle size distribution $D_{50}$ 1.72 µm and $D_{90}$ 4.09 µm.

The micronized product was spread on a tray and placed into a drying chamber at a temperature of 70° C. and vacuum maintaining conditions for 6 hours.

Figure 1:
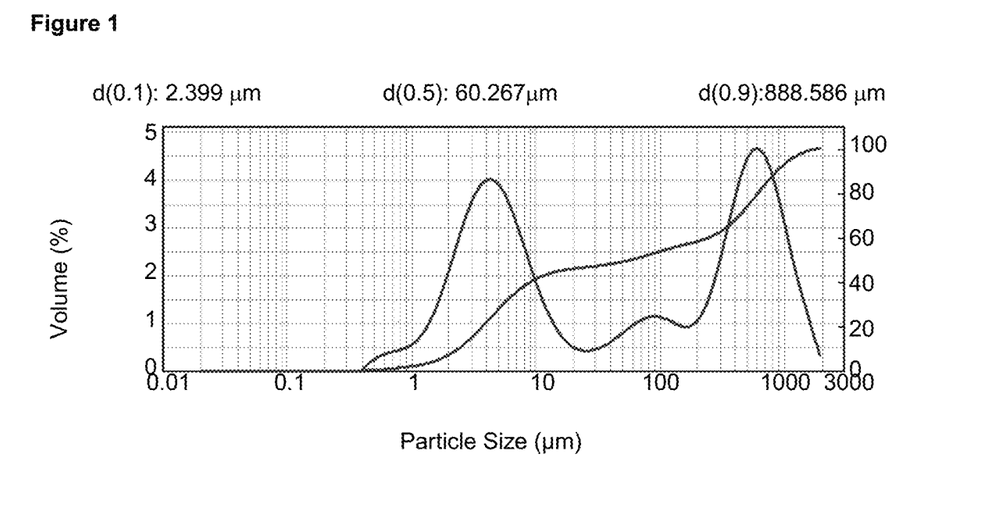
FIG. 1 shows the particle size distribution (PSD) by Malvern laser diffraction of a micronized glycopyrronium bromide product obtained according to the prior art (Example 1) after storage at 25° C. for 1 month.

After the curing step, the material was analysed and 1.8 wt. % of amorphous content was present, as determined by DVS. Moreover, significant amount of agglomerated material could also be observed. Particle size distribution (PSD) likewise changed after the curing step, as determined by LDS. As shown in FIG. 1, two additional populations (indicating agglomerated material) appeared after the curing step, with values of $D_{50}$ 60.27 µm and $D_{90}$ 888.59 µm.

Example 2: Preparation of Glycopyrronium Bromide 400 g of crystalline glycopyrronium bromide was micronized at room temperature in an ALPINE Pharma Multi-Processing System 100 AFG/100 AS micronizer with integrated GLOVE-BOX at a micronization pressure of 5 bar obtaining a particle size distribution $D_{50}$ 1.51 µm and $D_{90}$ 3.55 µm.

The micronized product was spread on a tray and placed into a vacuum oven (Kendro model VT 6130P-BL) at a temperature of 130° C. and vacuum conditions (pressure of below 50 mbar) without agitation or movement. The conditions were maintained for 4 hours.

Figure 2:
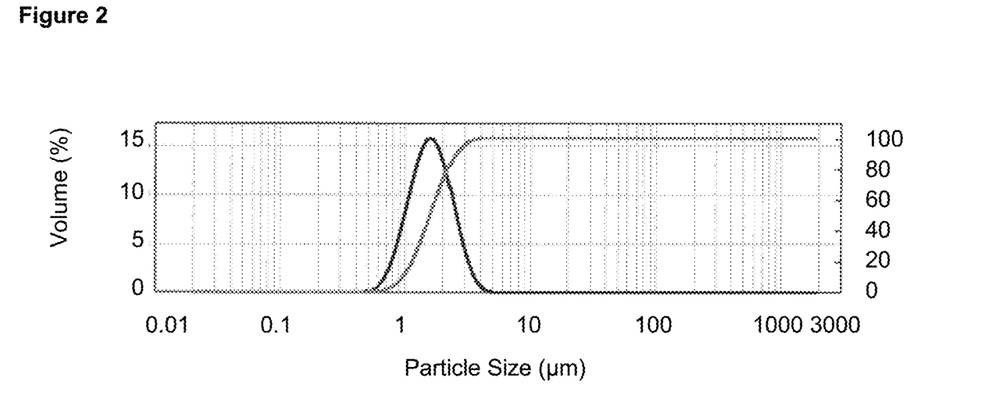
FIG. 2 shows the particle size distribution (PSD) by Malvern laser diffraction of a micronized glycopyrronium bromide product obtained according to a process of the invention (Example 2) after storage at 25° C. for 1 month.
Figure 3:
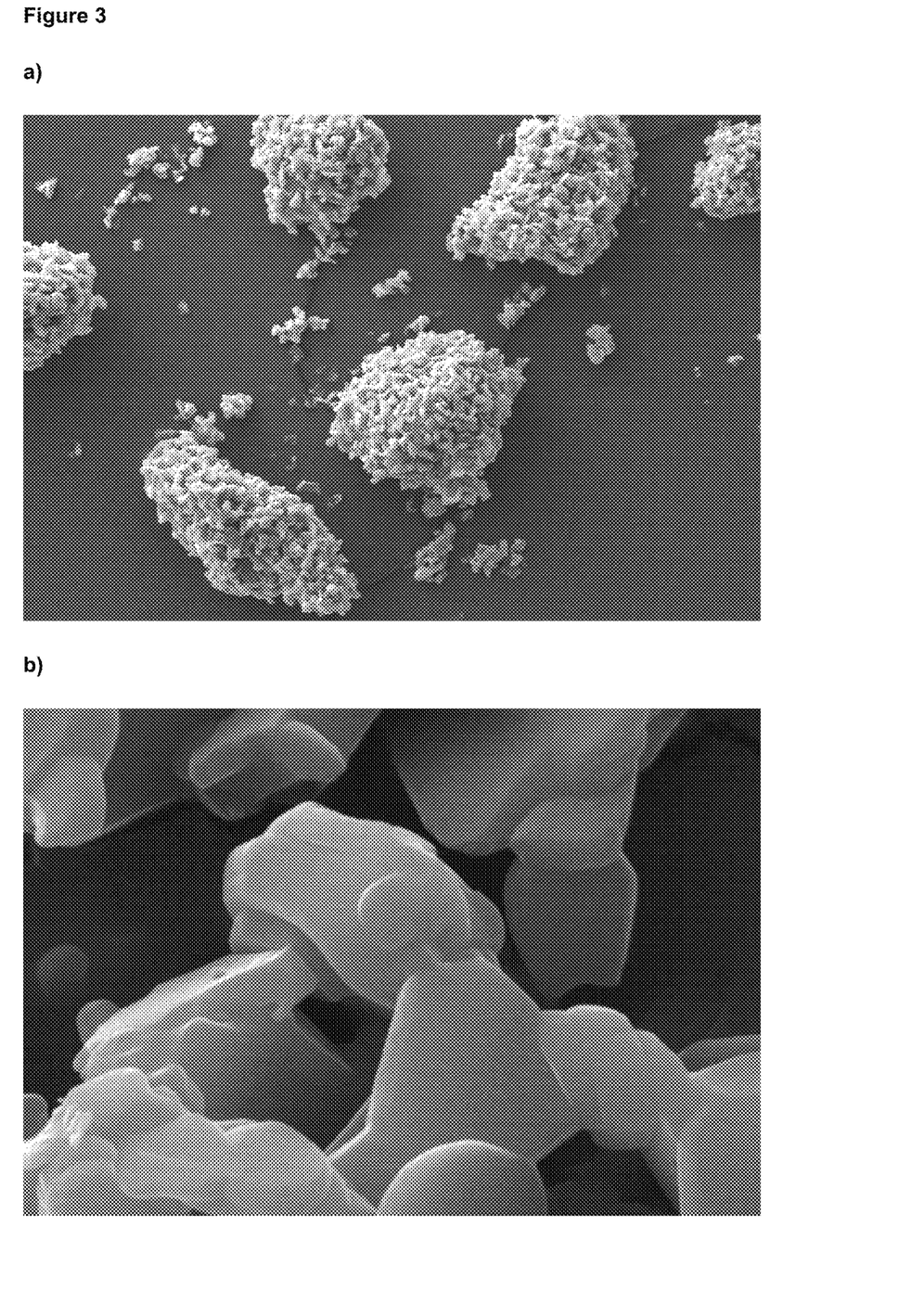
FIG. 3 in panels a) and b) shows SEM pictures of the product obtained from Example 1 (heated for 6 hours at 70° C.) on different scales.
Figure 4:
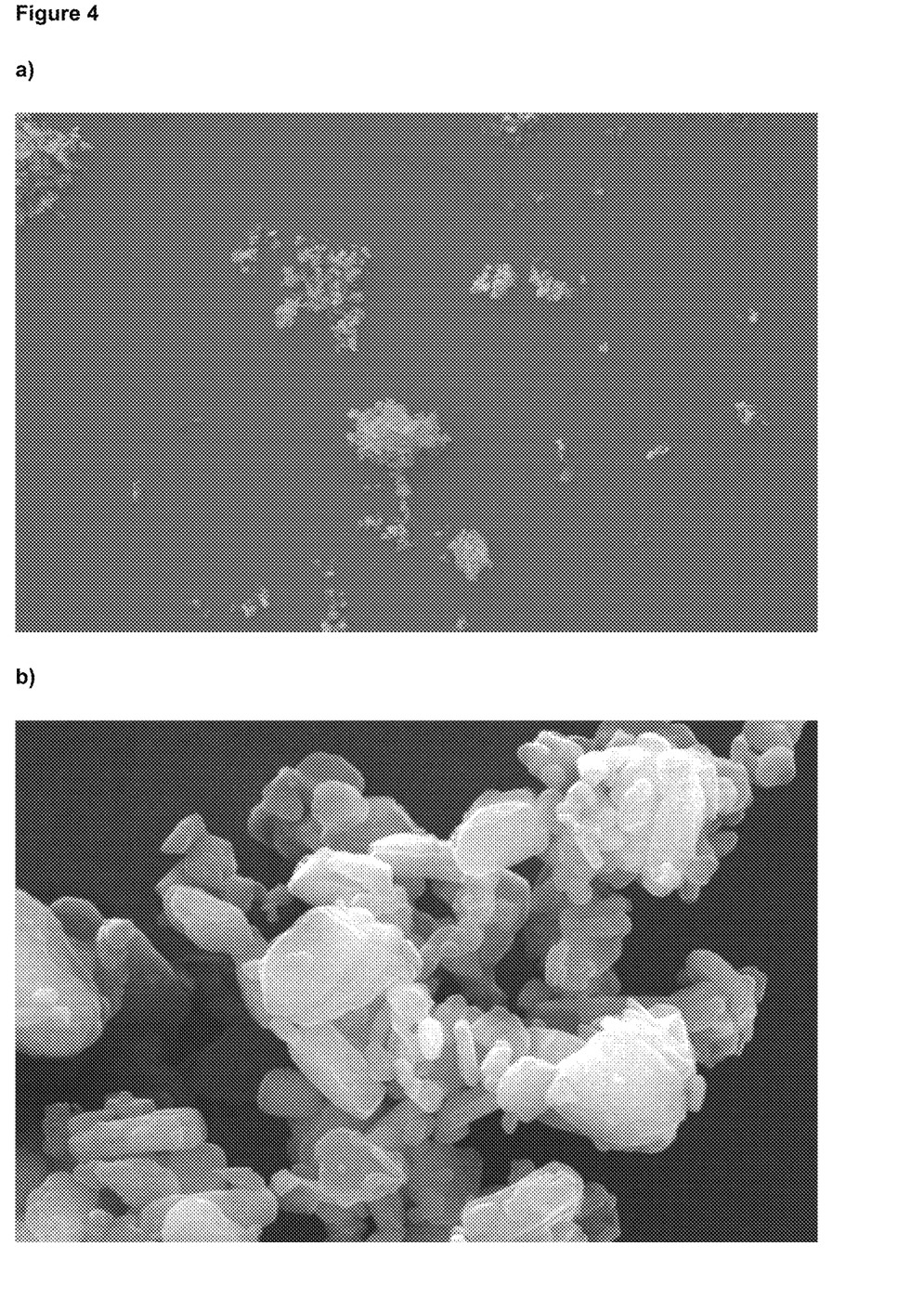
FIG. 4 in panels a) and b) shows SEM pictures of the product obtained from Example 6 (heated for 24 hours at 130° C.) on different scales.
Figure 5:
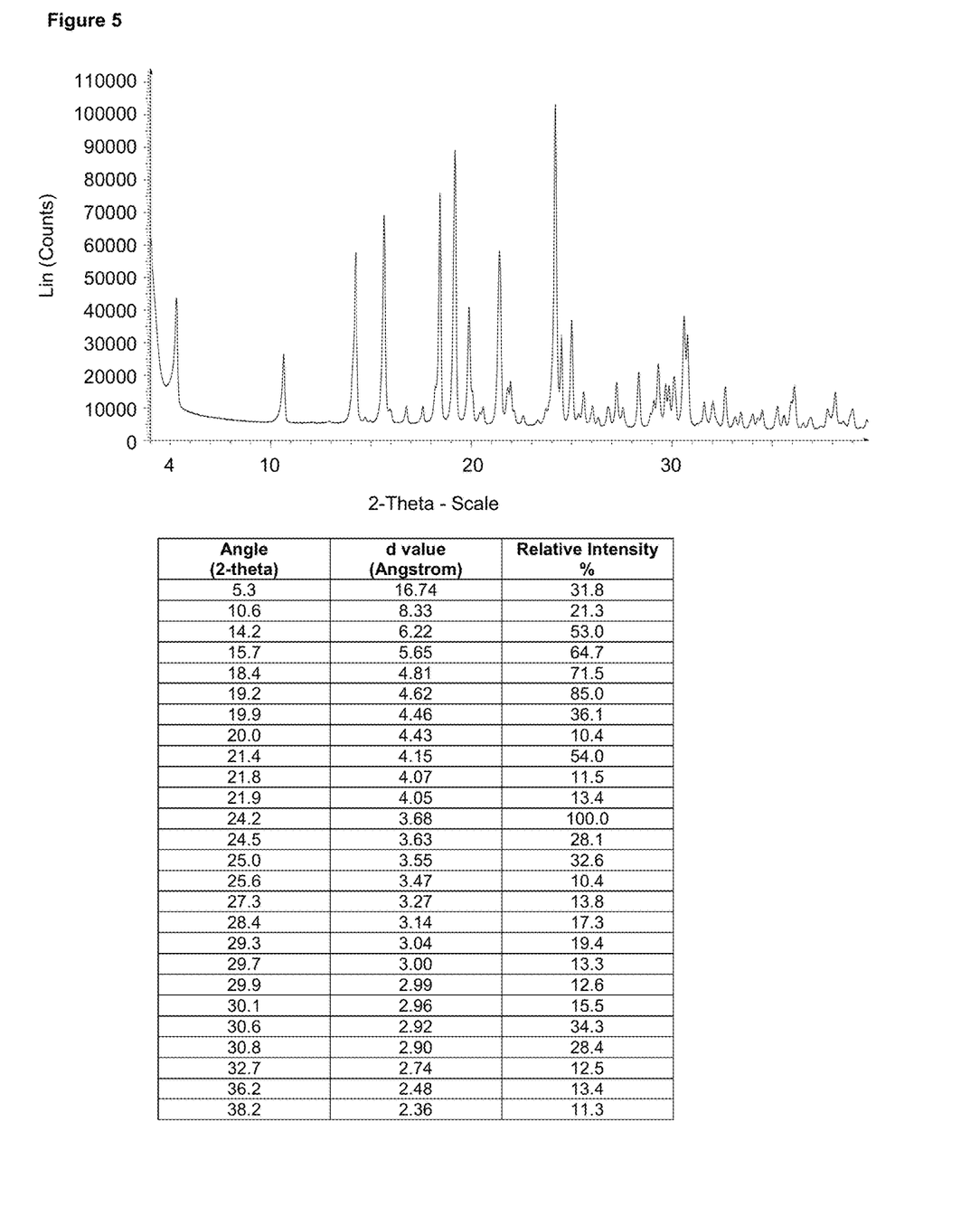
FIG. 5 shows a reference XRPD diffraction pattern of crystalline glycopyrronium bromide, including a peak list with relative intensities.

No amorphous content was detected, as determined by DVS and no agglomerated material was observed. The particle size distribution determined by LDS ($D_{50}$ 1.45 µm and $D_{90}$ 3.39 µm) remained stable after storage at 25° C. for (at least) 1 month, as indicated in FIG. 2. The micronized and stabilized glycopyrronium bromide showed no changes in chemical and polymorphic purity, even after prolonged storage at 25° C.

Example 3: Preparation of Glycopyrronium Bromide 400 g of crystalline glycopyrronium bromide was micronized at room temperature in an ALPINE Pharma Multi-Processing System 100 AFG/100 AS micronizer with integrated GLOVE-BOX at a micronization pressure of 5 bar obtaining a particle size distribution $D_{50}$ 1.51 µm and $D_{90}$ 3.55 µm.

The micronized product was spread on a tray and was placed into an oven (Kendro model VT 6130P-BL) at a pressure of 1 atm and at a temperature of 130° C. without agitation or movement. The conditions were maintained for 4 hours.

No amorphous content was detected, as determined by DVS, and no agglomerated material was observed. The PSD remained stable after storage at 25° C. for (at least) 1 month, as determined by LDS ($D_{50}$ 1.46 µm and $D_{90}$ 3.36 µm). The micronized and stabilized glycopyrronium bromide showed no changes in chemical and polymorphic purity.

Example 4: Preparation of Glycopyrronium Bromide 400 g of crystalline glycopyrronium bromide was micronized at room temperature in an ALPINE Pharma Multi-Processing System 100 AFG/100 AS micronizer with integrated GLOVE-BOX at a micronization pressure of 5 bar obtaining a particle size distribution $D_{50}$ 1.51 µm and $D_{90}$ 3.55 µm.

The micronized product was spread on a tray and was placed into a vacuum oven Kendro model VT 6130P-BL at a temperature of 130° C. and vacuum conditions (pressure of below 50 mbar) without agitation or movement. The conditions were maintained for 6 hours.

No amorphous content was detected, as determined by DVS, and no agglomerated material was observed. The PSD remained stable after storage at 25° C. for (at least) 1 month, as determined by LDS ($D_{50}$ 1.45 µm and $D_{90}$ 3.26 µm). The micronized and stabilized glycopyrronium bromide showed no changes in chemical and polymorphic purity.

Example 5: Preparation of Glycopyrronium Bromide 400 g of crystalline glycopyrronium bromide was micronized at room temperature in an ALPINE Pharma Multi-Processing System 100 AFG/100 AS micronizer with integrated GLOVE-BOX at a micronization pressure of 5 bar obtaining a particle size distribution $D_{50}$ 1.51 µm and $D_{90}$ 3.55 µm.

The micronized product was spread on a tray and was placed into a vacuum oven Kendro model VT 6130P-BL at a temperature of 130° C. and vacuum conditions (pressure of below 50 mbar) without agitation or movement. The conditions were maintained for 12 hours.

No amorphous content was detected, as determined by DVS, and no agglomerated material was observed. The PSD remained stable after storage at 25° C. for (at least) 1 month, as determined by LDS ($D_{50}$ 1.43 µm and $D_{90}$ 3.28 µm). The micronized and stabilized glycopyrronium bromide showed no changes in chemical and polymorphic purity.

Example 6: Preparation of Glycopyrronium Bromide 400 g of crystalline glycopyrronium bromide was micronized at room temperature in an ALPINE Pharma Multi-Processing System 100 AFG/100 AS micronizer with integrated GLOVE-BOX at a micronization pressure of 5 bar obtaining a particle size distribution $D_{50}$ 1.51 µm and $D_{90}$ 3.55 µm.

The micronized product was spread on a tray and was placed into a vacuum oven Kendro model VT 6130P-BL at a temperature of 130° C. and vacuum conditions (pressure of below 50 mbar) without agitation or movement. The conditions were maintained for 24 hours.

No amorphous content was detected, as determined by DVS, and no agglomerated material was observed. The PSD remained stable after storage at 25° C. for (at least) 1 month, as determined by LDS ($D_{50}$ 1.48 µm and $D_{90}$ 3.11 µm). The micronized and stabilized glycopyrronium bromide showed no changes in chemical and polymorphic purity.

The invention claimed is:

1. A process for obtaining stable glycopyrronium bromide, comprising the following steps:
    a) micronizing glycopyrronium bromide to obtain a particle size distribution (PSD) characterized by a $D_{90}$ of equal to or below about 10 µm; and
    b) curing the micronized glycopyrronium bromide by maintaining the product for at least 2 hours at a temperature of between 125° C. and 160° C.;
    wherein the micronization of glycopyrronium bromide in step a) is carried out in the absence of excipients and other active ingredients; and
    wherein the curing step b) is carried out under a pressure of below 1 atm.

2. The process according to claim 1, wherein the micronization of step a) is carried out until glycopyrronium bromide has a $D_{90}$ of equal to or below 8 µm.

3. The process according to claim 1, wherein the micronization of step a) is carried out until glycopyrronium bromide has a $D_{50}$ of equal to or below 6 µm.

4. The process according to claim 1, wherein the micronization of step a) is carried out at a pressure of equal to or below 8 bar.

5. The process according to claim 1, wherein the micronization of step a) is carried out at a temperature of between −10° C. and 30° C.

6. The process according to claim 1, wherein the micronized glycopyrronium bromide is maintained in the curing step b) at a temperature of between 125° C. and 160° C. for at least 3 hours.

7. The process according to claim 1, wherein the temperature in step b) is maintained between 125° C. and 150° C.

8. Glycopyrronium bromide, obtained by the process according to claim 1.

9. A composition comprising the glycopyrronium bromide according to claim 8, optionally comprising one or more further active ingredients and/or pharmaceutically acceptable excipients.

10. A method for the treatment of a patient suffering from asthma, COPD, or cystic fibrosis, comprising administering to said patient (i) the glycopyrronium bromide according to claim 8, or (ii) a composition comprising said glycopyrronium bromide according to claim 8, optionally comprising one or more further active ingredients and/or pharmaceutically acceptable excipients.

11. A dry powder inhaler device, or a capsule or a blister comprising (i) the glycopyrronium bromide according to claim 8, or (ii) a composition comprising said glycopyrronium bromide according to claim 8, optionally comprising one or more further active ingredients and/or pharmaceutically acceptable excipients.

12. The process according to claim 1, wherein the micronizing of step a) is carried out (i) until glycopyrronium bromide has a $D_{90}$ of equal to or below 8 µm, (ii) at a pressure of equal to or below 8 bar, and (iii) at a temperature of between −10° C. and 30° C.

13. The process according to claim 1, wherein the micronizing of step a) is carried out (i) until glycopyrronium bromide has a $D_{50}$ of equal to or below 6 µm, (ii) at a pressure of equal to or below 8 bar, and (iii) at a temperature of between −10° C. and 30° C.

14. The process according to claim 1, wherein the micronizing of step a) is carried out until glycopyrronium bromide has a $D_{50}$ of equal to or below 5 µm.

15. The process according to claim 1, wherein the micronizing of step a) is carried out at a pressure of equal to or below 5 bar.

16. The process according to claim 1, wherein the micronizing of step a) is carried out at a temperature of between 10° C. and 25° C.

17. The process according to claim 1, wherein the micronized glycopyrronium bromide is maintained in the curing step b) at a temperature of between 130° C. and 150° C. for at least 4 hours.

18. The process according to claim 1, wherein the curing step b) is carried out under a pressure below 500 mbar.

* * * * *